United States Patent [19]

Handelsman et al.

[11] Patent Number: 4,877,738
[45] Date of Patent: Oct. 31, 1989

[54] BIOLOGICAL CONTROL OF DAMPING OFF AND ROOT ROT AND INOCULUM PREPARATION THEREFOR

[75] Inventors: Jo Handelsman, Madison; Ellen H. Mester, Oregon; Lynn Wunderlich, Appleton, all of Wis.

[73] Assignee: Wisconsin Alumni Research Foundation, Madison, Wis.

[21] Appl. No.: 890,402

[22] Filed: Jul. 25, 1986

[51] Int. Cl.$^4$ .................... C12R 1/07; C12R 1/125
[52] U.S. Cl. .................... 435/252.5; 71/3; 71/77; 71/103; 424/92; 424/93; 424/115; 435/172.1; 435/254; 530/379
[58] Field of Search ............ 435/29, 172.1, 242, 435/253, 254, 834, 839, 252.5; 424/92, 93, 115; 71/3, 77, 103; 530/379

[56] References Cited

U.S. PATENT DOCUMENTS 4,250,170 2/1981 Kawaguchi et al. ............... 424/181
4,663,162 5/1987 Kado et al. ........................ 424/92

FOREIGN PATENT DOCUMENTS 0193608 9/1986 European Pat. Off. .

OTHER PUBLICATIONS

Gagné, S and Antoun, H. "Inhibition de Champignons phytopathogènes par des bactéries idolées du sol et de la rhizosphève de legumineuses", Can, J. Microbiol., vol. 31, 1985, pp. 856–860.

Hutchins, A. S. "In Vitro Inhibition of Root Rot Pathogens Phellinus–weirii, Armillariella mellea, Fomes-annosus, and hytophthora cinnamomi by a Newly Isolated Bacillus sp," Microb. Ecol, vol. 6 (3), 1980, pp. 253–260. (Biosis Abstracts).

Campbell and Clor, "Soil Moisture Affects the Interaction Between Gaeumannomyces Graminis var. Tritici and Antagonistic Bacteria," *Soil Biol. Biochem.*, vol. 17, No. 4, pp. 441–446 (1985).

*Primary Examiner*—Robert A. Wax
*Attorney, Agent, or Firm*—Quarles & Brady

[57] ABSTRACT

The invention includes substantially pure cultures of ATCC 53522 and mutants thereof effective in protecting plants from damping off the root rot as determinable by a defined plant protection assay. The invention further includes a protecting toxin produced by the bacteria just referred to. A seed inoculum includes an effective quantity of the bacteria or the toxin in a carrier. A method for protecting plants from damping off and root rot includes placing an effective quantity of the bacteria or toxin in the immediate vicinity of a plant to be protected.

5 Claims, No Drawings

BIOLOGICAL CONTROL OF DAMPING OFF AND ROOT ROT AND INOCULUM PREPARATION THEREFOR

TECHNICAL FIELD

The present invention relates to combatting damping off and root rot in plants and, in particular, to doing so by means of biological control.

BACKGROUND OF ART

Certain plants, of which alfalfa, soybeans, and common beans are examples, suffer from disease conditions called "damping off" and "root rot." The symptoms of damping off include the desiccation and subsequent death of seedlings soon after germination. Root rot symptoms include chlorosis and wilt of leaves and yellow to brown lesions with diffuse margins on roots and stems. The lesions can eventually lead to girdling and subsequent root decay resulting in decreased robustness in the plant or even in death. Often plants suffering from root rot begin by showing such symptoms, which may be mistaken as symptoms of drought and starvation. Such plants may be more vulnerable than healthy plants to attack by other pathogens, which are then mistaken as the cause of the death of the plants.

Damping off and root rot are merely two different sets of symptoms caused by infection of the plant by the same fungi and, in particular, by members of the Phytophthora, Pythium, Aphanomyces, and Fusarium genera. Thus, *Phytophthora megaspema* f. sp. medicaginis (hereinafter "Pmm") causes both damping off and root rot in alfalfa when soils are wet in most parts of the world where alfalfa is grown, and *Phytophthora Magasperma* f. sp. glycinea has been shown to cause root rot in soybeans under wet growing conditions. However, members of the other genera listed also are believed to attack alfalfa and soybeans. Root rot in common beans is believed caused by a complex of fungi including members of more than one of the genera referred to.

In general, control of damping off and root rot has been attempted by breeding for resistant plants. However, completely resistant cultivators have not been developed so that damping off and root rot remain major causes of crop loss. This is especially true under chronically wet growing conditions or when the same crop is planted repeatedly in the same fields. Certain fungicides such as metalaxyl partially control root rot. However, such fungicides are fairly expensive. For some crops, such as alfalfa, their use is not economically feasible. Also, resistance of the fungi to the fungicides can develop rapidly.

"Biological control" is defined as pathogen control by the use of a second organism. Mechanisms of biological control are diverse. For example, certain enteric bacteria have been examined for their usefulness in biological control of root rot in alfalfa. It is believed that control is obtained by competition between the enteric bacteria and the fungi for space on the surface of the alfalfa roots. In contrast, a toxin produced by one species of bacteria may be used to control another species of bacteria that appears as a pathogen. Bacterially produced antibiotics are an example of such toxins. The toxin can be isolated from the species producing it and administered directly, as is the common procedure with penicillin, or the species itself may be administered under appropriate circumstances to produce the toxin in situ.

Those skilled in the art are not cognizant of a biological control agent effective against a wide variety of fungus species that cause damping off and root rot in plants.

BRIEF SUMMARY OF THE INVENTION

The culture of the present invention is summarized as a substantially pure culture of ATCC 53522. An alternative culture of the invention is a substantially pure culture of a protecting mutant of ATCC 53522, the terms "protecting" being used in the manner defined below. The term "substantially pure" is similarly defined below. The culture of the invention is further summarized as a bacterial culture consisting essentially of bacteria selected from the group consisting of ATCC 53522, a protecting mutant of ATCC 53522, a mixture of any such mutants, and a mixture of any such mutants and ATCC 53522.

The protecting toxin of the invention is a protecting toxin selected from the group consisting of the protecting toxin produced by ATCC 53522, a protecting toxin produced by a protecting mutant of ATCC 53522, and a mixture of any such protecting toxins.

The seed inoculum of the invention for application to seeds to be protected from damping off includes a carrier and an effective quantity of bacteria carried thereby and selected from the group consisting of ATCC 53522, a protecting mutant of ATCC 53522, a mixture of any such mutants, and a mixture of any such mutants and ATCC 53522. An alternative seed inoculum for application to seeds to be protected from damping off includes a carrier and an effective quantity of a protecting toxin produced by ATCC 53522, a protecting toxin produced by a protecting mutant of ATCC 53522, and any mixture of such toxins.

The method of the invention for protecting plants in a growing medium from damping off and root rot includes placing in the growing medium in the immediate vicinity of the plant to be protected an effective quantity of bacteria selected from the group consisting of ATCC 53522, a protecting mutant of ATCC 53522, a mixture of any such mutants, and a mixture of any such mutants and ATCC 53522. An alternative method of the invention for protecting plants in a growing medium from damping off and root rot includes placing in the growing medium in the immediate vicinity of the plant to be protected an effective quantity of a protecting toxin selected from the group consisting of the protecting toxin produced by ATCC 53522, the protecting toxin produced by a protecting mutant of ATCC 53522, and any combination of such toxins. The term "immediate vicinity" is defined below.

DETAILED DESCRIPTION OF THE PREFERRED EMBODIMENT

A bacterial strain has been isolated from soil that exerts biological control over species of fungi responsible for damping off and root rot in plants. The strain has been deposited in the American Type Culture Collection, given the designation ATCC 53522, and shall hereinafter be referred to as "ATCC 53522". It has further been discovered that certain mutants of ATCC 53522 also provide biological control comparable to that provided by ATCC 53522. These bacteria have been obtained in substantially pure cultures. A "substantially pure" culture shall be deemed a culture of a bacteria containing no other bacterial species in quantities sufficient to interfere with replication of the culture. In addition, it has been discovered that the biological control is exerted by means of a toxin produced by the disclosed bacterial strains.

The method by which such control may be verified to exist is the "plant protection assay" detailed below. "Biological control" of fungi causing damping off and root rot shall be deemed to exist if, when an effective quantity of ATCC 53522, its mutants that exhibit biological control, or the anti-fungal toxin produced by them is placed in the soil or other growing medium in the immediate vicinity of the plant to be protected, a statistically significant reduction in the symptoms of damping off or root rot occurs. An "effective quantity" to combat damping off and root rot shall be that quantity sufficient to result in such a statistically significant reduction of symptoms. Clearly, if no quantity of a bacteria or any toxin produced thereby is an effective quantity as so defined, that bacteria and its toxins are not capable of exerting biological control over the fungi causing damping off and root rot. ATCC 53522 and those of its mutants capable of exerting such biological control shall sometimes be referred to collectively as "protecting" bacteria. Plants, including seeds, seedlings, and mature plants, treated with such an effective quantity of protecting bacteria or their toxins shall be referred to as "protected" from root rot or damping off.

ATCC 53522 was one of some 500 bacteria strains isolated from alfalfa roots and accompanying soil obtained from fields at the University of Wisconsin Experimental Farms at Arlington and Marshfield, Wisconsin, and from two private farms at Verona and Cross Plains, Wisconsin. The roots were cut into 1 cm segments, and each segment was placed in 10 ml of sterile, distilled water. The root segment and water then were sonicated at 20% maximum power with a Vibra-Cell 250 watt sonicator obtained from Sonics and Materials, Inc., Danbury, Connecticut. Sonication was continued for 15 seconds. The sonicated mixture then was diluted in sterile, distilled water, and the dilutions were placed on trypticase soy agar (hereinafter referred to as "TSA") in petri plates to form dilution plates. TSA contains 30 g/l trypticase soy broth (hereinafter referred to as "TSB") obtained from BBL Microbiology Systems, Inc., Cockeysville, Maryland, and 15 g/l agar. TSA and TSB are conventional bacterial culture media well known to those skilled in the art.

The dilution plates were incubated at 28° C. for two days. For each root sample, bacterial colonies were selected from the dilution plate that had the highest number of distinguishable colonies. One colony of each visually distinguishable morphology on the plate was sampled with a sterile loop and was plated on a new TSA culture plate to allow the development of colonies in plates free from contamination by other bacteria. After two days incubation at 28° C., a single colony was selected from the resulting bacterial growth and was used to inoculate a TSA slant. The resulting slant cultures were stored at 4° C. until they were screened by the plant protection assay disclosed below.

Five hundred different slant cultures were obtained by this method. As a consequence of the isolation procedure just reviewed, it was extremely unlikely that any of these 500 cultures were immediate siblings. However, fewer than 500 separate bacterial species were isolated. For example, a number of different cultures were obtained of bacteria whose colonies had the appearance of *Bacillus cereus*, including the culture identified above as ATCC 53522. However, each of these cultures had been obtained from a different root segment, and the root segments themselves were obtained from fields from four different geographical locations. Consequently, the chances that a single strain was present in more than one slant culture are very small. This fact is confirmed by the appearance of ATCC 53522 in only one of the 500 cultures.

Each of the cultured isolates that were obtained by the procedure just described were screened for their ability to protect alfalfa seedlings from damping off caused by Pmm. Initial screening was performed on the cultivar Iroquois, which is known to be vulnerable to Pmm. One gram of Iroquois alfalfa seeds was soaked in 18 M sulfuric acid for 10 minutes. The seeds were then washed in 2 l of sterile distilled water and were placed in 10 ml of sterile water and shaken at 28° C. for 24 hours. Next the seed coats were removed manually with forceps, and the seedlings were planted in test tubes containing 5 ml sterile, moist vermiculite. Three seedlings were planted in each test tube. Two days after the seedlings were planted, each test tube was inoculated with 0.3 ml of a two-day-old culture of the bacterial isolate to be tested. These cultures had been grown to saturation in TSB and had sporulated. Then each tube immediately was inoculated with $10^3$ zoospores of Pmm. The Pmm zoospores had been produced by the method of S. A. Miller (1982) "Cytological and Biochemical Factors Involved in the Susceptible, Host Resistant and Non-host Resistant Interactions of Alfalfa with *Phytophthora megasperma*," Ph.D. thesis, University of Wisconsin. By this method, a sample of a colony of Pmm was transferred to an agar media on which it could grow. Conventional V8 media was used, consisting of 200 ml V8 vegetable juice, 2.5 g $CaCO_3$, and 15 g agar in 800 ml water. However, any agar media such as conventional tomato juice agar or carrot agar encouraging the growth of the fungus would be sufficient. The sample of the fungus colony was incubated at 24° C. for 4 days and ten at 28° C. for an additional 3 days. A growing colony of Pmm developed. The agar around the colony was excised to leave a section of undisturbed agar with the growing fungus on it surrounded by a "moat" formed by the excision of agar. This moat was filled with sterile water to the level of the agar that had not been excised. The plate was incubated at 16° C. for one hour, whereupon the water was replaced, and the plate was incubated at 16° C. for an additional 5 hours. Zoospores were released from the fungus into the water of the moat. The concentration of zoospores in the water was measured with a hemacytometer, and a sample of the water was diluted with additional sterile water at 16° C. to reach a final concentration of zoospores of $10^4$/ml.

After addition of the zoospores, the test tubes containing the plants were incubated at 24° C. with a 12 hour photoperiod for 5 days, at which time the plants were evaluated for symptoms of damping off. Using Pmm and the cultivator Iroquois, all control plants consistently were dead. Thus, the fact that a plant survived at all was evidence of biological control exerted by the bacterial isolate used. All bacteria that demonstrated that minimal amount of effectiveness for biological control were retested by this same method to verify the consistency of such control. The screening procedure just described constitutes a particular example of the plant protection assay described more generally below.

Of the 500 isolates from the 4 sites in Wisconsin referred to above, only ATCC 53522 strain was identified as having the ability consistently to exert biological control of Pmm in Iroquois alfalfa, as evidenced by at least 20 separate experiments. The level of control was such that alfalfa seedlings subjected to such control under the conditions of the screening procedure were visually indistinguishable from alfalfa seedlings that had never been exposed to Pmm. ATCC 53522 appears to be *Bacillus cereus,* based on physiological tests, its colony morphology, and its spore size, shape, and position. Thus, ATCC 53522 produces acetoin, forms an acid from glucose broth, hydrolyzes starch, and grows in anaerobic agar. These characteristics, together with colony morphology, and spore size, shape, and position observed in ATCC 53522 are cited as distinctively characteristic of *Bacillus cereus* by R. E. Buchanan and N. E. Gibbons, co-editors (1974), *Bergey's Manual of Determinative Bacteriology,* 8th Edition, pp. 532–535.

*Bacillus cereus* is a not uncommon bacterium in field soils. However, strains of *Bacillus cereus* demonstrating antifungal activity are almost unheard of. The inventors tested two known strains of *Bacillus cereus* obtained from entirely separate sources and found neither of them to exhibit the anti-fungal properties of ATCC 53522. Furthermore, of the 500 root-associated bacteria reviewed in the isolation process, many were probably *Bacillus cereus* and, in fact, many of them had the same colony morphology as ATCC 53522. However, none of these other strains exhibited the antifungal qualities of ATCC 53522. S. Wakayama, et al. (1984), *Antimicrob. Agents Chemother.,* 26, 939–940, describe antifungal activity in a strain of *Bacillus cereus.* However, most of the antifungal antibiotics are made by *Bacillus subtilus,* which is easily distinguishable from ATCC 53522. The antifungal toxin produced by ATCC 53522 differs from that of the reported strain of *Bacillus cereus* referred to in that the toxin is of lower molecular weight and has different solubility properties. In addition, ATCC 53522 differs from the reported *Bacillus cereus* strain in that it grows anaerobically whereas the reported strain does not. Consequently, it is clear that the two *Bacillus cereus* strains are not the same and that their toxins are not the same.

The following is the disclosure of the plant protection assay whereby a test material such as a bacteria, a toxin, or the like may be tested for its ability to exert biological control over a fungus capable of causing the symptoms of damping off or root rot. The seed of the plant to be protected is planted in a planting medium in the presence of damping off or root rot causing fungi. The planting medium may be a damp soil containing such fungi, vermiculite in water with the fungi present either in the vermiculite and water or in or on the seed, or any other planting medium in which the seed will grow and the fungi may freely develop. The bacteria, toxin, or other test material is placed at least in the immediate vicinity of the seed. Such placement shall be understood to be in the "immediate vicinity" of the seed if any soluble test material or any soluble exudate of a bacteria being tested will be in actual contact with the seed as it germinates.

Preferably the seed is coated with the test material, and when the test material is so used with respect to a seed, it shall be referred to hereinafter as a "seed inoculum." The process of coating seed with a seed inoculum is generally well known to those skilled in the art, and any conventional method that does not require conditions sufficiently harsh to kill bacteria or destroy toxins or other materials included in the seed inoculum is adequate. An easy and preferred method is to suspend or dissolve the test material in a 1.5% aqueous solution of methyl cellulose. For convenience, it will be presumed hereinafter that the seed inoculum is a bacteria suspended in the methyl cellulose, although a dissolvable material such as a bacterial toxin may be handled in the same manner. The plant seed to be protected is added to the suspension and is mixed vigorously with it to coat the surface of the seed with the suspension. The seed may then be dried aseptically, preferably by being placed within a laminar flow hood on a sterile surface such as a sterile petri plate. The result is a dry, seed inoculum-coated seed. When the coated seed is planted in the planting medium, the test material accompanies it to reside in the immediate vicinity of the seed.

After a time sufficient for seedling growth and the expression of the symptoms of damping off, seedlings developing from the planted seed may be evaluated for visual evidence of protection, when compared to controls. In strains of alfalfa, soybeans, and snap beans known to be vulnerable to damping off, 2 weeks of growing time in a growth chamber at 24° C. with a 12 hour photoperiod was found to be a period sufficient for the expression of symptoms of damping off when seedlings were being grown in test tubes containing roughly $10^3$ zoospores of Pmm or comparable, damping off-causing fungi. Protected seeds developed into seedlings visually indistinguishable from uninfected seeds while control seedlings developing from unprotected seeds were killed or, in the case of snap beans, exhibited brown lesions on roots and stems, stunted roots, rotted roots, and other visually apparent symptoms of root rot.

Protecting mutants of ATCC 53522 include both naturally occurring and artificially induced mutants. For example, ATCC 53522 is generally sensitive to the antibiotics rifampicin and neomycin. However, naturally occurring mutants of ATCC 53522 were isolated that exhibited resistance to one or the other of these antibiotics. Certain of these mutants, as well as one naturally occurring mutant distinguishable from the parent ATCC 53522 strain by the appearance of its colonies, are discussed in the Examples below and were found to protect alfalfa plants in the plant protection assay. Other mutants of ATCC 53522 were artificially induced by subjecting ATCC 53522 to the mutagen N-methyl-nitrosoguanidine in conventional ways, as is discussed in the Examples below. Most of these induced mutants also were found to protect alfalfa plants in the plant protection assay.

As has been disclosed above, it has been further discovered that an active anti-root rot toxin is produced by ATCC 53522 and those of its mutants that are characterized by their abilities to protect plants from root rot in the plant protection assay. The toxin may be collected from growth media in which the bacteria has been cultured. The toxin is effective to protect plants from damping off and root rot even when separated from the bacteria producing it and applied to seed and to seedlings that have been placed in a planting medium containing root rot causing fungi. As is shown in the Examples below, the effectiveness of the application of the toxin is demonstrable by the plant protection assay, with the toxin being substituted for a protecting bacteria. Thus, the invention further includes such toxins and a seed inocula containing effective quantities of the toxin isolatable from ATCC 53522 and its protecting mutants. The toxin may be isolated from ATCC 53522 and its protecting mutants by filtering the bacteria from the culture media in which they have been grown to a saturated culture or in any event to a sporulated culture. Other conventional purification and concentration steps may be undertaken as may be considered convenient or desirable, so long as the toxin remains active, as may be demonstrated by the plant protection assay.

The chemical nature and mechanism of protective action of the toxin are not fully known. However, the inventors have tentatively identified as the toxin, a molecule appearing in the culture media of ATCC 53522 and its protecting mutants when their cultures have sporulated. The molecular weight of the molecule is less than 1,000. The toxin is soluble in methanol and binds both to anion and cation exchange columns. The toxin is stable for at least ten minutes when heated as high as 100° C. at pH 7.0, but the toxin becomes inactive upon heating for as little as ten minutes to 80° C. at either pH 2.0 or pH 10.0. The toxin is also stable for at least three months at 4° C. and for at least three days at 25° C. The toxin causes visual changes in zoospores of Pmm. When the zoospores are treated with the toxin in aqueous solution, they deform within ten minutes. The zoospores so treated do not germinate on laboratory media, do not swim, and in all respects appear to be dead.

The inoculum of the invention for the protection of plants from damping off and root rot includes a quantity of bacteria in an innocuous carrier, the bacteria being selected from the group consisting of ATCC 53522 and those of its mutants exhibiting the ability to protect plants against damping off and root rot, as determinable by the plant protection assay. Consistent with the discussion above, such mutants will be referred to as "protecting mutants." A carrier shall be deemed "innocuous" if it neither inhibits growth of the bacteria nor is harmful when applied to the plants to be protected. A 1.5% aqueous solution of methyl cellulose is a preferred innocuous carrier. The inoculum may be made simply by mixing the bacteria from a mature culture with the carrier. A "mature" culture shall be a culture that has sporulated. A culture of the bacteria that has grown for two days at 30° C. on either a TSA plate or in TSP generally has matured.

An alternative embodiment of the inoculum of the invention comprises a quantity of the anti-root rot toxin disclosed above held in a carrier harmless to the plants to be treated and to the toxin. Preferred carriers include water and a 1.5% methyl cellulose aqueous solution.

The method of the invention for protecting plants from damping off and root rot is to apply a quantity of bacteria effective to inhibit root rot to the immediate vicinity of the plant to be protected. The bacteria so applied must be ATCC 53522 or one of its protecting mutants. The application may be accomplished by coating the seed with the bacteria by any conventional means, by directly applying the bacteria to the soil or other planting media in which the plant is growing or the like. Application by coating the seed is the preferred method. An alternative embodiment of the method just disclosed is the application of a quantity of the anti-root rot toxin effective to inhibit damping off and root rot to the immediate vicinity of the plant to be protected. As disclosed above, the toxin must be isolated from ATCC 53522 or its protecting mutants. Once again, the application may be accomplished by coating the seed with the anti-root rot toxin, by applying it directly to the soil or other planting media in which the plant is growing, or the like.

The examples below provide specific examples of the invention as broadly disclosed herein, although the invention is not to be understood as limited in any way to the terms and the scope of the examples.

EXAMPLE 1

Plant Protection Assay of ATCC 53522 Using Alfalfa

The screening procedure disclosed above was repeated as an application of the plant protection assay to test the protective ability of ATCC with alfalfa. The cultivar of alfalfa used was Iroquois. The fungus used was Pmm. One gram of seeds was soaked in 18M sulfuric acid for ten minutes, washed in 2 l of sterile distilled water, placed in 10 ml of sterile distilled water, and shaken at 28° C. for 24 hours. Thereafter, the seed coats were removed with forceps, and the seedlings were planted in test tubes containing 5 ml of moist vermiculite. Three seedlings were planted in each test tube. After two days, each test tube was inoculated with 0.3 ml of a two day old culture of ATCC 53522 that had been grown in TSB to saturation. Thereafter, each tube was inoculated with $10^3$ zoospores of Pmm. The plants then were incubated at 24° C. with a 12 hour photo period for 5 days, whereupon the plants were evaluated for viability. All of the control seedlings were dead. The seedlings that had been treated with ATCC 53522 had the appearance of normal seedlings that had not been exposed to Pmm.

EXAMPLE 2

Plant Protection Assay of ATCC with Soybeans

The procedure of Example 1 was repeated with soybeans of the variety McCall substituted for the alfalfa seeds and zoospores of *Phytophthora megasperma* f. sp. *glycinea* substituted for the zoospores of Pmm. Instead of being planted in test tubes, the soybean seeds were planted in 10 ml plastic cones having holes in the bottom, and the cones were placed in a pan of water. The seedlings were examined for protection two weeks after inoculation with the zoospores. Ten out of 10 controled seedlings were killed by the fungus. All of the seedlings that had been treated with ATCC 53522 survived with healthy, white roots.

EXAMPLE 3

Plant Protection Assay of ATCC 53522 with Snap Beans

The procedure of Example 3 was repeated with snap beans of the variety Early Gallatin, and the fungi used were naturally occurring fungi present in a soil sample from the University of Wisconsin Experimental Station at Hancock, Wisconsin. All of the control seedlings developed root rot symptoms within two weeks, including brown lesions on roots and stems, stunted roots, and rotted roots. The seedlings that had been treated with ATCC 53522 developed no root rot symptoms in the same period of time.

EXAMPLE 4

Field Test of ATCC 53522

Alfalfa seeds of the cultivar Iroquois were mixed in a suspension of ATCC 53522 in 1.5% methyl cellulose. The bacteria had been cultured on a TSA plate that had been incubated at 30° C. for two days, by which time the culture had sporulated. The culture then was scraped into 3 ml of the 1.5% methyl cellulose solution to provide the suspension of bacteria. One gram of alfalfa seeds was added to this suspension and was mixed thoroughly therewith. The seed then was spread on sterile petri plates and dried overnight in a laminar flow hood. The coated seeds were planted in circular plots 0.3 m in diameter at Marshfield, Wisconsin. Owing to dry growing conditions, both emergence of plants and evidence of Pmm damping off were poor. Nevertheless, emergence in a control, untreated plot was 18% whereas in the plot planted with bacterium-treated seed, emergence was 30%. An additional plot was planted with seed that had been coated with a fungicide, metalaxyl, a conventional control agent for damping off. In that plot, emergence was 2.9%. Thus, it is apparent that ATCC 53522 can protect alfalfa in the field as effectively as does metalaxyl. Furthermore, symptoms of root rot became apparent in the control plot having untreated seeds as the growing season proceeded. No symptoms of root rot appeared in the plot planted with the seeds coated with ATCC 53522.

EXAMPLE 5

Plant Protection Assay of ATCC 53522 Toxin

The method of Example 1 was repeated with ATCC 53522 being replaced with a filtrate of a culture of that bacterium. The filtrate was prepared by centrifuging a two day old, saturated broth culture at 10,000 g for ten minutes and then filtering the resulting supernatant twice through 0.45 μm filters. The filtrate was stored at −20° C. before being applied in the plant protection assay identically to the way the bacteria had been applied in the experiment reported as Example 1. The protective effect observed in treated alfalfa seedlings versus untreated seedlings was identical to that reported in Example 1.

EXAMPLE 6

Spontaneous Mutants of ATCC 53522

Spontaneously developing antibiotic resistant mutants of ATCC 53522 were isolated by plating a culture derived from a colony of ATCC 53522 on media containing an antibiotic to which ATCC 53522 normally is sensitive. Several resistant colonies developed. They were each sampled with a sterile toothpick and replated on the antibiotic-containing media. The mutants were then tested in the plant protection assay by the procedure described in Example 1. Five mutants were developed that were resistant to rifampicin. A sixth mutant was developed that was resistant to neomycin. Each of the mutants protected alfalfa plants in the plant protection assay as applied in Example 1 as effectively as did ATCC 53522.

EXAMPLE 7

Induced Mutants of ATCC 53522

A culture of vegetatively growing cells of ATCC 53522 was prepared and diluted to a density of $10^8$ cells/ml. A quantity of this culture was treated by exposure to 1 μg/ml N-methyl-nitrosoguanidine for thirty minutes at room temperature. The cells then were washed with water and dilution plates were prepared on TSA. The treatment with N-methyl-nitrosoguanidine had killed 99% of the bacteria in the original culture. Thus, the remaining viable bacteria each had a high probability of containing at least one mutation. Of 500 such bacteria derived from independent colonies, 490 were able to protect alfalfa plants against Pmm when tested by the method of Example 1.

It will be apparent to those skilled in the art that a number of modifications and changes can be made without departing from the spirit and scope of the present invention. Therefore, it is not intended that the invention be limited by the terms of the general disclosure above nor by the Examples but only by the claims, which follow.

What is claimed is:

1. A biologically pure culture of *Bacillus cereus* having the identifying characteristics of ATCC 53522.

2. A biologically pure culture of a mutant strain derived from *Bacillus cereus* ATCC 53522 retaining the capability of producing a plant protecting toxin effective to protect plants against pathology from *Phytophthora megasperma*.

3. A biologically pure bacterial culture consisting essentially of bacteria selected from the group consisting of *Bacillus cereus* ATCC 53522, mutant of *Bacillus cereus* ATCC 53522 retaining the capability of producing a plant protecting toxin effective against *Phytophthora megasperma*, a mixture of any such mutants, and a mixture of any such mutants and *Bacillus cereus* ATCC 53532.

4. A seed inoculum for application to seeds to be protected from damping off fungal plant disease comprising a carrier and an effective quantity of protecting bacteria selected from the group of bacteria consisting of *Bacillus cereus* ATCC 53522, a mutant of *Bacillus cereus* ATCC 53522 retaining the capability to produce a plant protecting toxin effective against *Phytophthora megasperma*, a mixture of such mutants, and a mixture of *Bacillus cereus* ATCC 53522 and such mutants, the inoculum being substantially soil-free.

5. A method for protecting plants in a growing medium from damping off and root rot fungal plant disease comprising placing in the growing medium in the immediate vicinity of the plant to be protected an effective quantity of bacteria selected from the group consisting of *Bacillus cereus* ATCC 53522, mutants of *Bacillus cereus* ATCC 53522 retaining the capability to produce a plant protecting toxin effective against *Phytophthora megasperma*, a mixture of such mutants, and a mixture of such mutants with *Bacillus cereus* ATCC 53522.

* * * * *